US009827045B2

United States Patent
Hongo et al.

(10) Patent No.: US 9,827,045 B2
(45) Date of Patent: Nov. 28, 2017

(54) LASER WAVEGUIDE DEVICE AND LASER WAVEGUIDE SYSTEM

(71) Applicant: J. Morita Mfg. Corporation, Kyoto (JP)

(72) Inventors: Akihito Hongo, Kyoto (JP); Katsumi Hiyoshi, Kyoto (JP); Masato Wada, Kyoto (JP)

(73) Assignee: J. Morita Mfg. Corporation, Kyoto (JP)

( * ) Notice: Subject to any disclaimer, the term of this patent is extended or adjusted under 35 U.S.C. 154(b) by 190 days.

(21) Appl. No.: 14/727,628

(22) Filed: Jun. 1, 2015

(65) Prior Publication Data

US 2015/0349480 A1  Dec. 3, 2015

(30) Foreign Application Priority Data

May 30, 2014 (JP) ................................. 2014-111887

(51) Int. Cl.
*H01S 3/00* (2006.01)
*A61B 1/06* (2006.01)
(Continued)

(52) U.S. Cl.
CPC ............ *A61B 18/24* (2013.01); *G01J 1/4257* (2013.01); *A61B 2018/00166* (2013.01);
(Continued)

(58) Field of Classification Search
CPC ......... A61B 18/24; A61B 18/20; A61B 18/22; A61B 2018/2005; A61B 2018/2035;
(Continued)

(56) References Cited

U.S. PATENT DOCUMENTS 4,604,992 A * 8/1986 Sato .......................... A61B 1/05
348/67
6,821,245 B2 * 11/2004 Cline ................. A61B 1/00009
600/160

(Continued)

FOREIGN PATENT DOCUMENTS

JP  2008-509756 A  4/2008
JP  2010-051650 A  3/2010
JP  4459724 B2     4/2010

OTHER PUBLICATIONS

Notification of Reasons for Refusal issued in corresponding Japanese Application No. 2014-111887, dated Jan. 31, 2017 (7 pages).

(Continued)

*Primary Examiner* — John Lee
(74) *Attorney, Agent, or Firm* — Osha Liang LLP (57) ABSTRACT

A laser light waveguide device includes laser light provision units that oscillate and cause laser light to exit; a laser light waveguide path formed of an optical fiber capable of guiding the laser light; and a control unit that controls the laser light provision units. The control unit detects an illumination spot (output of the visible laser light) based on a captured image, captured by an image capturing unit, of a laser light illumination area and an area close thereto illuminated with the laser light, and controls exit of the infrared laser light by the infrared laser light provision unit based on a result of detection of the illumination spot (output of the visible laser light).

7 Claims, 6 Drawing Sheets

(51) Int. Cl.
　　　*A61B 18/24*　　(2006.01)
　　　*G01J 1/02*　　(2006.01)
　　　*G01J 1/04*　　(2006.01)
　　　*H01S 3/16*　　(2006.01)
　　　*H01S 3/223*　　(2006.01)
　　　*H01S 3/23*　　(2006.01)
　　　*G01J 1/42*　　(2006.01)
　　　*A61B 18/00*　　(2006.01)

(52) U.S. Cl.
　　　CPC .......... *A61B 2018/00642* (2013.01); *A61B 2018/00672* (2013.01); *A61B 2018/00702* (2013.01); *A61B 2018/00708* (2013.01); *A61B 2018/00982* (2013.01)

(58) Field of Classification Search
　　　CPC .... A61B 2018/2205; A61B 2018/2222; A61B 2018/2227; A61B 2018/2233; A61B 2018/2211; A61B 2018/00166; A61B 2018/00642; A61B 2018/00648; A61B 2018/00666; A61B 2018/00672; A61B 2018/00696; A61B 2018/00702; A61B 2018/00708; A61B 2018/00982; H01S 3/0014; G01J 2001/4257; G01J 1/4257
　　　See application file for complete search history.

(56) References Cited

U.S. PATENT DOCUMENTS

| | | | | |
|---|---|---|---|---|
| 8,280,099 B2 * | 10/2012 | Harrison | ............ | B23K 26/032 |
| | | | | 382/100 |
| 8,473,035 B2 * | 6/2013 | Frangioni | ............ | A61B 5/415 |
| | | | | 600/476 |
| 8,506,613 B2 * | 8/2013 | Webb | ................. | A61N 5/0618 |
| | | | | 607/88 |
| 8,636,726 B1 * | 1/2014 | Wells | .................. | A61B 18/22 |
| | | | | 372/10 |
| 2002/0103439 A1 * | 8/2002 | Zeng | ................. | G01J 3/0289 |
| | | | | 600/476 |
| 2006/0052661 A1 * | 3/2006 | Gannot | ................. | A61B 1/042 |
| | | | | 600/108 |
| 2008/0015553 A1 * | 1/2008 | Zacharias | ............ | A61F 9/008 |
| | | | | 606/4 |
| 2008/0044178 A1 * | 2/2008 | Harrison | ............. | B23K 26/032 |
| | | | | 398/17 |
| 2009/0009595 A1 * | 1/2009 | Ishiwata | ............ | A61B 1/00165 |
| | | | | 348/68 |
| 2009/0264768 A1 * | 10/2009 | Courtney | ............ | A61B 5/0062 |
| | | | | 600/463 |
| 2009/0299354 A1 * | 12/2009 | Melsky | ................. | A61B 18/245 |
| | | | | 606/16 |
| 2010/0004513 A1 * | 1/2010 | MacKinnon | ............ | A61B 1/05 |
| | | | | 600/180 |
| 2010/0076304 A1 * | 3/2010 | Teramura | ............... | A61B 3/102 |
| | | | | 600/425 |
| 2010/0168515 A1 * | 7/2010 | Sugimoto | ............ | A61B 1/0008 |
| | | | | 600/109 |
| 2010/0228132 A1 * | 9/2010 | Brennan | ............... | A61B 5/0066 |
| | | | | 600/478 |
| 2011/0063427 A1 * | 3/2011 | Fengler | .............. | A61B 1/00186 |
| | | | | 348/65 |
| 2011/0082451 A1 * | 4/2011 | Melsky | ................. | A61B 18/24 |
| | | | | 606/14 |
| 2013/0216114 A1 * | 8/2013 | Courtney | ............. | A61B 5/0066 |
| | | | | 382/130 |
| 2013/0289358 A1 * | 10/2013 | Melsky | ................. | A61B 18/24 |
| | | | | 600/249 |
| 2015/0349480 A1 * | 12/2015 | Hongo | ................. | A61B 18/24 |
| | | | | 250/227.2 |

OTHER PUBLICATIONS

Notification of Reasons for Refusal issued in corresponding Japanese Application No. 2014-111887, dated Sep. 5, 2017 (6 pages).

* cited by examiner

IMAGE DISPLAY UNIT

FIG.6

LASER WAVEGUIDE DEVICE AND LASER WAVEGUIDE SYSTEM

TECHNICAL FIELD

The present invention relates to a laser waveguide device and a laser waveguide system for guiding infrared laser light usable in, for example, medical and industrial fields.

BACKGROUND ART

Infrared laser light, which has a high energy output and is absorbed much into water, is useful for industrial laser processing devices and also for medical laser scalpels. Especially, devices using infrared laser light such as Er-YAG laser light oscillating at a wavelength of 2.94 μm, $CO_2$ laser light oscillating at a wavelength of 10.6 μm, or the like are used as products in medical and industrial fields.

In the industrial fields, such infrared laser light is used for cutting various materials, welding, and surface modification. In the medical field, such infrared laser light is used for the purpose of incision, coagulation, transpiration, hemostasis and the like of biological tissues. Infrared laser light used in these fields has a significantly high energy output than laser light used in information and communication fields.

Infrared laser light used in the medical and industrial fields has a high energy output as described above, and is invisible. Therefore, a waveguide path of such infrared laser light needs to be monitored in real time regarding soundness to prevent breakage or any other flaw, and also needs to be sufficiently safe even when any flaw occurs.

For example, in order to prevent infrared laser light, which is invisible laser light, from illuminating an unintended position or in order to monitor the soundness of the waveguide path, infrared laser light and visible light are superimposed on each other. In this way, the position illuminated with the infrared laser light is specified and thus the infrared laser light is prevented from illuminating an unintended position.

Quartz-based optical fibers, which are widely used for information and communication purposes and illumination purposes, cannot be used as a waveguide path for infrared laser light having a wavelength of 2 μm or longer, such as Er-YAG laser light or $CO_2$ laser light mentioned above. Therefore, fluoride-based optical fibers, silver halide-based optical fibers, chalcogenide-based optical fibers and the like, which are formed of a material transmissive of light in an infrared light wavelength region, are used.

However, the fluoride-based optical fibers can merely guide infrared laser light having a wavelength of about 3 to 4 μm at the longest and thus cannot be used as a waveguide path for $CO_2$ laser light. The silver halide-based optical fibers and the chalcogenide-based optical fibers can guide infrared laser light having a longer wavelength but cannot guide visible laser light.

The silver halide-based optical fibers also have a problem of being sensitive to visible laser light having a short wavelength, resulting in silver being deposited to increase loss.

In the meantime, apart from these solid optical fibers, hollow optical fibers are used as an infrared light waveguide path. For the hollow optical fibers, a dielectric thin film coating a metal inner wall is set to have a thickness with which the reflectance is maximum for light in the wavelength region to be guided. Therefore, an appropriately designed hollow optical fiber can guide desired infrared laser light and also visible laser light.

In the medical and industrial fields, infrared laser light is used as an energy source that causes a physical or chemical change to a substance to be illuminated. Therefore, the infrared laser light is required to have a high energy output and a high guiding efficiency. By contrast, visible laser light is merely required to have a guiding efficiency with which the visible laser light is visually recognizable.

As described above, infrared laser light used in the medical and industrial fields is of a high energy output. Therefore, it is highly important for safety to guarantee that the waveguide path is sound. More specifically, for solid optical fibers, it is needed to consider the risk of end surface damage, melting, and rupture. In the case of hollow optical fibers, the risk of end surface damage is lower than in the case of solid optical fibers, but it is required to consider the risk of breakage, which may be caused by bending, melting, contamination with foreign substances, or the like.

According to an optical structure that has been put into practice as a measure for preventing infrared laser light from illuminating an unintended position as described above, a beam combiner is used on the exit side so that infrared laser light and visible light are superimposed on each other.

Specifically, visible light is guided by a conventional quarts-based optical fiber, whereas infrared laser light is guided by an infrared light waveguide path formed of a solid optical fiber or a hollow optical fiber, both of which are formed of an infrared light-transmissive material mentioned above. Namely, the optical structure in which a beam combiner is used on the exit side so that infrared laser light and visible light are superimposed on each other includes two waveguide paths. The central axis of the infrared laser light and the central axis of the visible light, both on an illumination target illuminated with the two types of laser light, are matched to each other by a beam combiner that combines the two types of light.

With the optical structure in which the invisible infrared laser light and the visible laser light are superimposed on each other on the exit side, the position illuminated with the infrared laser light can be visually recognized by visible laser light. Thus, the infrared laser light can be prevented from illuminating an unintended position. However, even in the case where the waveguide path of the infrared laser light is damaged, the visible laser light, which is guided by a waveguide path different from the waveguide path that guides the infrared light, normally exits. Therefore, the soundness of the waveguide path that guides the infrared invisible light cannot be checked.

A method for monitoring the soundness of the waveguide path is proposed by, for example, Patent Document 1. According to the method proposed by Patent Document 1, an outer circumferential surface of an optical fiber that guides laser light is covered with a conductive film. Electrical characteristics of the conductive film are changed in accordance with the state of breakage of the optical fiber. This is used to check the soundness of the optical fiber.

However, the method disclosed in Patent Document 1 requires formation of the conductive film on the outer circumferential surface of the optical fiber acting as a waveguide path and also requires a power supply device used to measure the electrical characteristics of the conductive film. This complicates the system structure and makes it difficult to construct a low-cost system.

In addition, according to the method proposed in Patent Document 1, the optical fiber used as the waveguide path is electrically conducted from an end on the light source side to an exit tip. When the optical fiber is used for an application in the medical field, the exit tip of the waveguide path approaches or even contacts a biological body. This may possibly cause electromagnetic hypersensitivity to the biological body.

Another method for monitoring the soundness of the waveguide path is proposed by, for example, Patent Document 2. According to the method proposed by Patent Document 2, laser light of a standard light amount is guided by a waveguide path, and the amount of the guided light is measured. When the measured value is lower than a threshold level, it is determined that the waveguide path has abnormality. In this case, the transmission of the laser light is stopped, so that the safety of the waveguide path is guaranteed.

The "standard light amount" is a safe light amount with which neither waveguide path nor the measurement device is broken. When the above-measured value is confirmed to be the threshold value or higher, the output of the laser light is increased to a desired level.

As described above, according to the method disclosed in Patent Document 2, the soundness of the waveguide path can be guaranteed in the case where light of an amount smaller than, or equal to, the standard amount is guided. However, in the case where laser light of a higher energy output is guided by the waveguide path, the waveguide path may be possibly broken by energy loss of the guided laser light itself.

As can be seen, with the method disclosed in Patent Document 2, even if the soundness of the waveguide path is confirmed in the case where laser light of an amount smaller than, or equal to, the standard amount is guided, the waveguide path may be broken when the output of the laser light is increased. It is not possible to monitor the soundness of the waveguide path in real time while laser light of a desired output level is caused to exit.

The above-mentioned threshold used to check the soundness when laser light of the standard light amount is guided is used with an assumption that a measured value is uniquely defined. However, the guiding efficiency of a waveguide path for laser light is changed by, for example, a bending state of the waveguide path, and thus is not necessarily a constant value. Especially in the case of a hollow optical fiber, a bending loss needs to be considered, and the threshold value for guaranteeing safety is changed by, for example, the state of installation of the waveguide path. Therefore, there may be a case where although the waveguide path is not damaged and is kept sound, the measured value is lower than the threshold value and thus the exit of the laser light is stopped. The threshold value needs to be adjusted in accordance with the state of use. Since such adjustment increases troublesome work imposed on a user, it is difficult for the user to adjust the threshold value in accordance with the state of use.

CITATION LIST

Patent Literature

Patent Document 1: Japanese Laid-Open Patent Publication No. 2010-51650
Patent Document 2: Japanese Patent No. 4459724

SUMMARY OF THE INVENTION

In one or more embodiments, the present invention provides a laser waveguide device and a laser waveguide system for monitoring, with a simple structure, the soundness of a laser waveguide path that guides infrared laser light of a high energy output, so that the infrared laser light is caused to exit safely.

In one or more embodiments, the present invention is directed to a laser light waveguide device including a laser light provision unit that oscillates and causes laser light to exit; a laser light waveguide path formed of an optical fiber capable of guiding the laser light; and a control unit that controls the laser light provision unit. The laser light includes invisible infrared laser light which is visually unrecognizable and visible laser light which is visually recognizable; and the control unit detects an output of the visible laser light based on a captured image, captured by an image capturing unit, of a laser light illumination area and an area close thereto illuminated with the laser light, and controls exit of the infrared laser light based on a result of detection of the output of the visible laser light. The present invention is also directed to a laser light waveguide system including the above-described laser light waveguide device; and the image capturing unit. The control unit controls the image capturing unit.

The laser light waveguide path may be formed of a hollow optical fiber.

The expression "detect an output of the visible laser light" encompasses: detecting an output of the visible laser light, detecting that there is no output of the visible laser light, and detecting an energy output of the visible laser light that is higher than, or equal to, a predetermined threshold level.

The expression "controls exit of the infrared laser light based on a result of detection of the output of the visible laser light" encompasses the following: controlling the oscillation itself of the infrared laser light, or shutting the exit of the oscillated infrared laser light by use of a shutter unit such as a shutter or the like to control the exit of the infrared laser light, either by detecting an output of the visible laser light or by detecting that there is no output of the visible laser light; a combination of control on the oscillation itself of the infrared laser light and control on exit of the infrared laser light by use of the shutter unit. For example, the exit of the infrared laser light may be controlled based on a detected output of the visible laser light. Alternatively, the exit of the infrared laser light may be controlled to be stopped upon detection that there is no output of the visible laser light. In this manner, the above-mentioned expression encompasses controlling the exit of the infrared laser light either by detecting an output of the visible laser light or by detecting that there is no output of the visible laser light.

According to one or more embodiments of the present invention, the soundness of the laser light waveguide path that guides the infrared laser light of a high energy output is monitored, so that the infrared laser light exits safely, with a simple structure.

This will be described in more detail. The invisible infrared laser light, which is visually unrecognizable, and the visible laser light, which is visually recognizable, are guided by the laser light waveguide path. Owing to this arrangement, the visible laser light is directed to a desired position, and thus the invisible infrared laser light, which is visually unrecognizable, is prevented from illuminating an unintended position.

The control unit detects the output of the visible laser light based on a captured image, captured by the image capturing element, of the laser light illumination area and the area close thereto illuminated with the laser light guided by the laser light waveguide path. Owing to this arrangement, the soundness of the laser light waveguide path is monitored in real time.

The exit of the invisible infrared laser light is controlled based on the detection result of the output of the visible laser light. Owing to this arrangement, when, for example, the laser light waveguide path is ruptured and is not sound, the output of the visible laser light guided by the laser light waveguide path is not detected. Namely, although the visible laser light is guided together with the invisible infrared laser light, which is visually unrecognizable, the output of the visible laser light is not detected. Based on this, the control unit determines that the laser light waveguide path is not sound and thus controls the exit of the invisible infrared laser light of a high energy output to be stopped. Therefore, a defect, for example, leak of the infrared laser light is prevented and the laser light waveguide system is used safely.

As described above, in the laser light waveguide device and the laser light waveguide system according to one or more embodiments of the present invention, the invisible infrared laser light, which is of a high energy output and is visually unrecognizable, and the visible laser light, are guided by the laser light waveguide path. Thus, the invisible infrared laser light is prevented from unexpectedly illuminating an unintended position. In addition, the output of the visible laser light is detected, and thus the soundness of the laser light waveguide path is checked in real time. Therefore, even if some abnormality, for example, breakage, occurs to the laser light waveguide path, the exit of the invisible infrared laser light of a high energy output is stopped, so that a human or a device located around the laser light waveguide device or the laser light waveguide system is protected against any risk and safety is guaranteed. This is realized with a simple structure with no need to provide any additional device such as a sensor or the like to the laser light waveguide path.

In an embodiment of the present invention, the laser light waveguide path may be formed of a hollow optical fiber.

According to one or more embodiments of the present invention, the invisible infrared laser light and the visible laser light are guided at a high guiding efficiency, and thus the output of the visible laser light is detected more certainly.

In an embodiment of the present invention, the laser light waveguide system may further include an illumination unit that illuminates the laser light illumination area and the area close thereto. The control unit may control the illumination unit; and the control unit may control an illumination cycle of the illumination unit so as to be synchronized with a detection cycle of detecting the visible laser light based on the captured image of the laser light illumination area and the area close thereto.

In an embodiment of the present invention, the laser light waveguide system may further include a filter that attenuates background light around the laser light illumination area.

In an embodiment of the present invention, the control unit may control the visible laser light to exit at a predetermined pulse cycle; and the control unit may control a detection cycle of detecting the visible laser light, based on the captured image of the laser light illumination area and the area close thereto, to be synchronized with a pulse cycle of causing the visible laser light to exit.

In an embodiment of the present invention, the image capturing unit may capture the image of the laser light illumination area and the area close thereto illuminated with the visible laser light at a pulse cycle; and the control unit may detect the visible laser light based on a difference between an output of the captured image when the visible laser light is caused to exit, and an output of the captured image when the visible laser light is not caused to exit.

In an embodiment of the present invention, the image capturing unit may include a wavelength filter that attenuates light in a visible light wavelength region except for an oscillation wavelength of the visible laser light.

According to one or more embodiments of the present invention, the output of the visible laser light guided by the laser light waveguide path is made more clearly distinguishable from the background light around the laser light illumination area. Therefore, the output of the visible laser light is detected more certainly.

The above-described filters may each be realized by a filtering process of attenuating a predetermined wavelength region by image processing, or may be realized by a physical filter formed of polarizer glass or the like.

In an embodiment of the present invention, the laser light waveguide system may further include an endoscope that allows the laser light waveguide path to be inserted thereinto and includes the image capturing unit.

According to one or more embodiments of the present invention, the soundness of the laser light waveguide path that guides the infrared laser light of a high energy output is monitored, while the invisible infrared laser light is caused to exit safely to be used for treatment in the medical field and for processing in the industrial fields.

In one or more embodiments, the present invention provides a laser waveguide device and a laser waveguide system for monitoring, with a simple structure, the soundness of a laser waveguide path that guides invisible infrared laser light of a high energy output, so that the invisible infrared laser light is caused to exit safely.

BRIEF DESCRIPTION OF DRAWINGS

FIG. 5 shows still another method for detecting an output of the visible laser light Ls.

DETAILED DESCRIPTION OF THE INVENTION

Embodiments of the present invention will be described with reference to the drawings.

Figure 1:
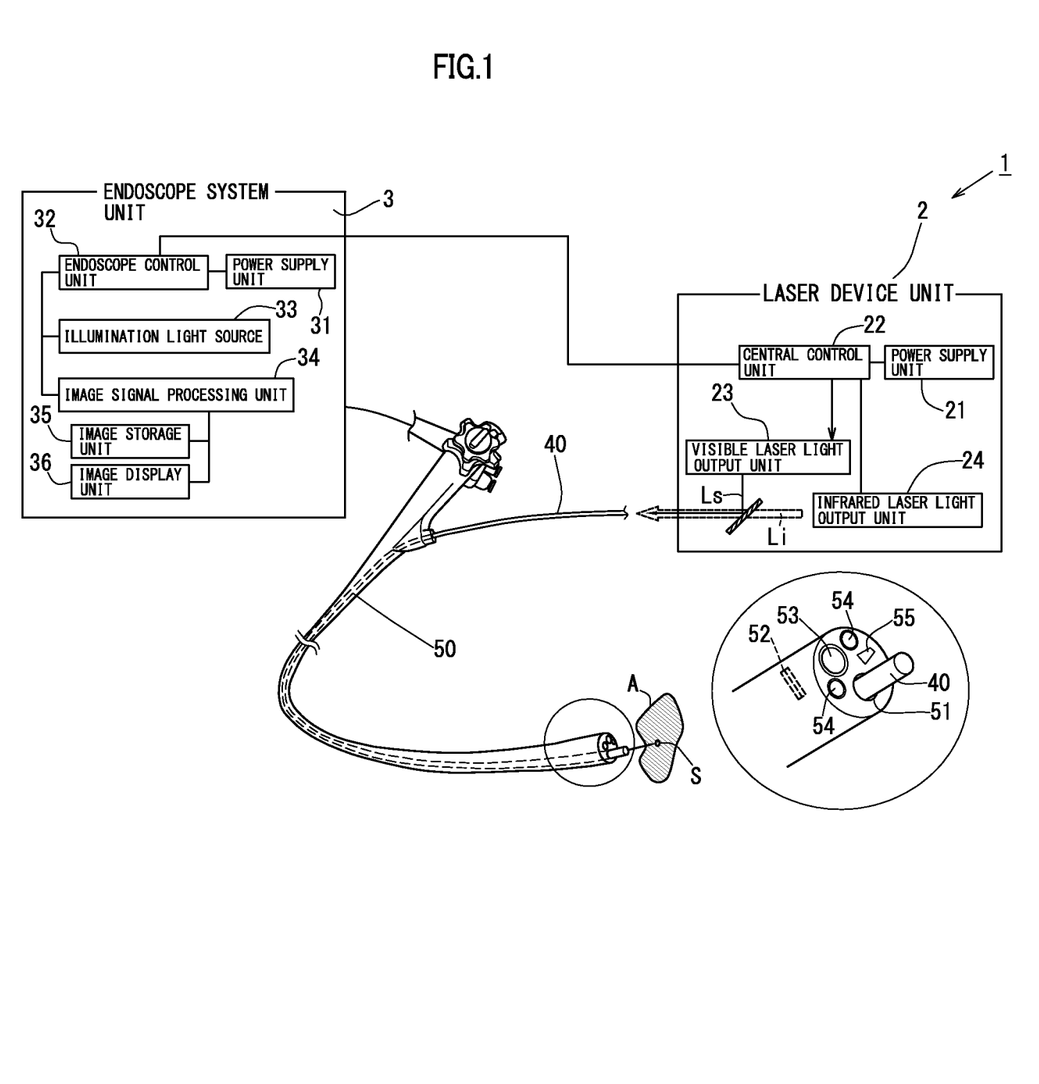
FIG. 1 is a schematic structural view of a laser light waveguide system 1 in an embodiment according to the present invention.
Figure 2A:
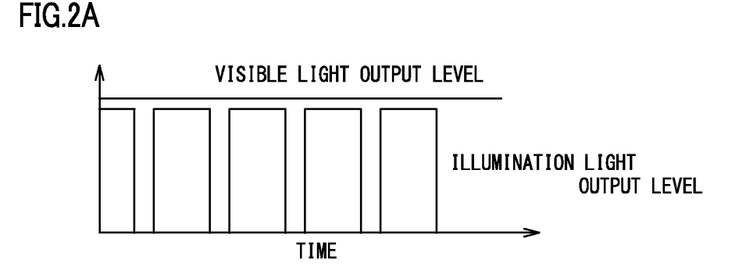
FIGS. 2A and 2B show a method for detecting an output of visible laser light Ls.
Figure 2B:
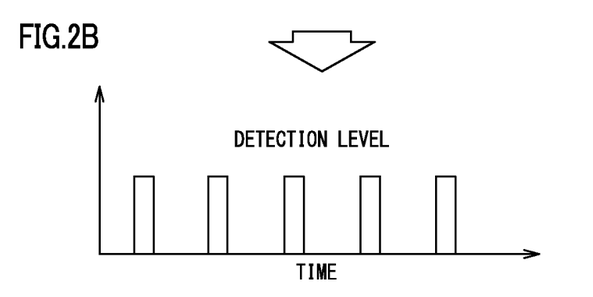
Figure 6:
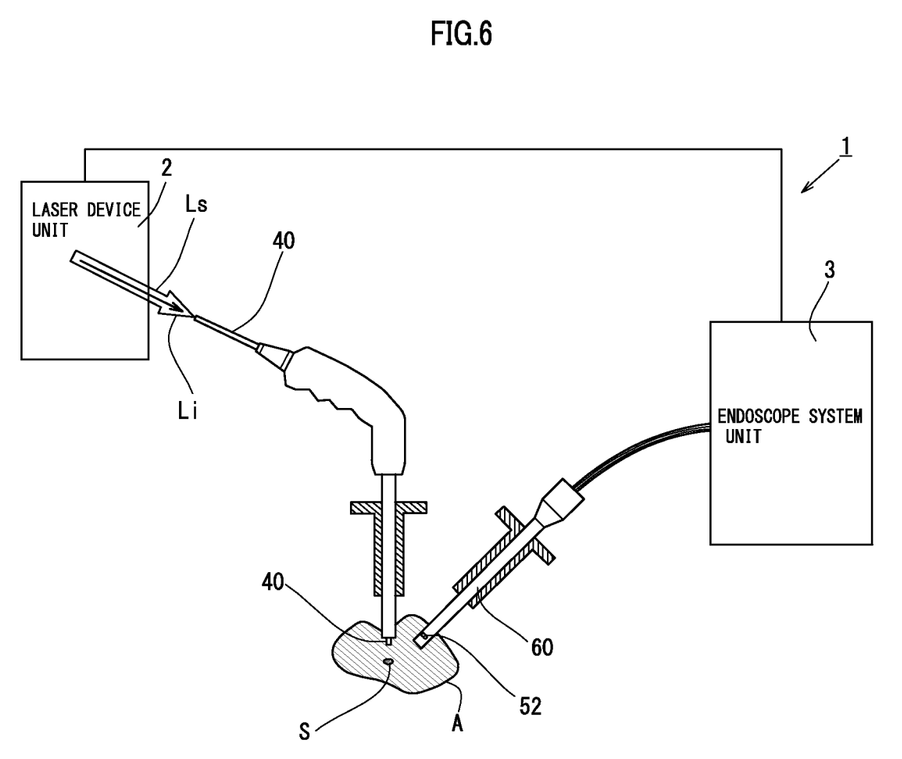
FIG. 6 is a schematic structural view of a laser light waveguide system 1 in another embodiment according to the present invention.

FIG. 1 is a schematic structural view of a laser light waveguide system 1 in an embodiment according to the present invention. FIGS. 2A and 2B show a method for detecting an output of visible laser light Ls. FIGS. 3A and 3B through FIG. 5 each show another method for detecting an output of the visible laser light Ls. FIG. 6 is a schematic structural view of a laser light waveguide system 1 in another embodiment according to the present invention.

The laser light waveguide system 1 includes a laser device unit 2, a laser light waveguide path 40, and an endoscope system unit 3.

The laser device unit 2 includes a power supply unit 21, a central control unit 22, a visible laser light provision unit 23 that oscillates and causes visible laser light Ls to exit, and infrared laser light provision unit 24 that oscillates and causes infrared laser light Li to exit. The visible laser light provision unit 23 and the infrared laser light provision unit 24 are connected to a central control unit 22, and exit of the visible laser light Li and the infrared laser light Ls by the visible laser light provision unit 23 and the infrared laser light provision unit 24 is controlled by the central control unit 22.

The visible laser light provision unit 23 oscillates and causes red or green visible laser light Ls to exit. In the case where red light is used, a semiconductor laser, which causes light to exit at a relatively high energy output and costs low, is usable. Green light is highly recognizable visually and is easily distinguishable from a biological tissue such as blood or the like.

The endoscope system unit 3 includes a power supply unit 31, an endoscope control unit 32, an illumination light source 33 that emits illumination light, an image signal processing unit 34, an image storage unit 35, an image display unit 36, and an endoscope 50. The illumination light source 33, the image signal processing unit 34, the image storage unit 35, and the image display unit 36 are connected to, and controlled by, the endoscope control unit 32.

The endoscope control unit 32 is connected to the central control unit 22 of the laser device unit 2, and controls the illumination light source 33 and the like under the control of the central control unit 22.

The image signal processing unit 34 is a processing unit that processes a captured image captured by an image capturing element 52 provided in the vicinity of a tip of the endoscope 50 described later, and thus stores the processed image on the image storage unit 35 and also causes the processed image to be displayed by the image display unit 36.

The endoscope 50 is lengthy and flexible. The endoscope 50 includes one or a plurality of channels 51, and also includes the image capturing element 52 provided in the vicinity of the tip thereof. (In FIG. 1, only one channel 51 is shown.) The image capturing element 52 operates via an objective lens 53. The endoscope 50 also includes a channel provided therein that is used to feed water or air, so that the water or air is ejected from a water/air feed nozzle 55. In addition, an illumination bundle optical fiber (not shown) is inserted into the endoscope 50 from the illumination light source 33 of the endoscope system unit 3. Thus, a laser light illumination area A and an area close thereto is illuminated via an illumination lens 54.

The image capturing element 52 captures an image of the laser light illumination area A and the area close thereto via the objective lens 53. The captured image is processed by the image signal processing unit 34 of the endoscope system unit 3 and displayed as the captured image by the image display unit 36. The image capturing unit 52 thus structured senses an illumination spot S of the visible light Ls guided by the laser light waveguide path 40.

The laser light waveguide path 40 is inserted into the channel 51 of the lengthy and flexible endoscope 50. The laser light waveguide path 40 is formed of a hollow optical fiber that is flexible and is capable of guiding both of the visible laser light Ls and the infrared laser light Li. Usually, a surgical treating tool such as a forceps or the like is inserted into a channel of an endoscope. By contrast, in this embodiment, the laser light waveguide path 40 is inserted into the channel 51 of the endoscope 50.

The visible laser light Ls and the infrared laser light Li respectively exit from the visible laser light provision unit 23 and the infrared laser light provision unit 24 included in the laser device unit 2. Optical axis of the two types of light are superimposed on each other in the laser device unit 2, and then the two types of light are guided in the same waveguide area in the laser light waveguide path 40.

In the laser light waveguide system 1 having the above-described structure, the visible laser light Ls that is oscillated and caused to exit by the visible laser light provision unit 23 is guided by the laser light waveguide path 40. As a result, the illumination spot S of the visible laser light Ls appears on the laser light illumination area A, which is an illumination target positioned forward to a tip of the laser light waveguide path 40. The illumination spot S is illuminated also with the infrared laser light Li. However, the infrared laser light Li is invisible and thus is not sensed by the image capturing element 52.

In the case where the illumination spot S appearing on the illumination target is detected by the image signal processing unit 34 based on the captured image captured by the image capturing element 52, the central control unit 22 determines that the laser light waveguide path 40 is sound with no damage such as rupture or the like. In this case, the central control unit 22 controls the infrared laser light provision unit 24 to superimpose the infrared laser light Li of a high energy output on the visible laser light Ls, so that the two types of light are guided by the laser light waveguide path 40.

In the case where the output of the visible laser light Ls is not sensed by the image capturing element 52, namely, in the case where the illumination spot S is not detected by the image signal processing device 34 based on the captured image captured by the image capturing element 52, the central control unit 22 determines that some abnormality has occurred to the laser light waveguide path 40. In this case, the central control unit 22 controls the infrared laser light provision unit 24 to stop the oscillation of the infrared laser light Li, or operates a shutter (not shown) to shut the infrared laser light Li, so that the exit of the infrared laser light Li is stopped.

In this manner, the laser light waveguide system 1 causes the visible laser light Ls to be guided by the laser light waveguide path 40 together with the infrared laser light Li. Thus, the infrared laser light Li is prevented from illuminating an unintended position, and also the soundness of the laser light waveguide path 40 is monitored in real time.

The illumination level of the visible laser light Ls is lower than the illumination level of the infrared laser light Li, which acts an energy source for medical treatment or processing. In general, a waveguide path for infrared laser light guides light in an infrared light wavelength region efficiently, but cannot guide light in a visible light region of a shorter wavelength, or even if can, guides the light at a much lower efficiency than the light of the infrared light wavelength region. The hollow optical fiber forming the laser light waveguide path 40 has a transmittance of about 80% for $CO_2$ laser light used as the infrared laser light Li while having a transmittance of several percent for red visible laser light Ls. Therefore, there may be cases where the output of the visible laser light Ls is not easily recognized visually when being displayed by the image display unit 36 included in the endoscope system unit 3. Especially in the case where the illumination light emitted from the illumination light source 33 to illuminate the laser light illumination area A and the area close thereto is too strong, or in the case where the color of the visible laser light Ls is similar to the color of a biological tissue such as blood or the like, the output of the visible laser light Ls and background light are difficult to be distinguished from each other.

In this case, as shown in FIG. 2A, the illumination light emitted from the illumination light source 33 to illuminate the laser light illumination area A and the area close thereto may be extinguished or weakened at a very short cycle, so that the cycle of extinguishing (weakening) the illumination light is synchronized with a detection cycle of detecting the visible laser light Ls. In this way, as shown in FIG. 2B, the output of the visible laser light Ls is made clearly distinguishable from the background light.

The visible laser light Ls does not need to be continuous as shown in FIG. 2A as far as exiting in a very short duration in which the illumination light from the illumination light source 33 is extinguished (weakened). The time durations in which the illumination light is extinguished (weakened) may be so short that the extinction (weakening) is not visually recognizable on the image display unit 36. Alternatively, the illumination light may be pulsed light which is turned on or off at too short a cycle to be recognized as being intermittent.

As described above, the visible laser light may be laser light that is oscillated and caused to exit in a specific wavelength region, for example, red laser light, green laser light or the like. The illumination light emitted from the illumination light source 33 may be white light, or may be light of wavelengths corresponding to red, green and blue that exit cyclically so as to be visually recognized as white light. Such illumination light, when being reflected by the illumination target and visually recognized as the background light, has a wide range of wavelengths. Therefore, light of the visual light wavelength region except for the wavelength of the visible laser light Ls can be attenuated by a wavelength filter. As a result, the output of the visible laser light Ls guided by the laser light waveguide path 40, namely, the illumination spot S, is made clearly distinguishable from the background light around the laser light illumination area A.

Figure 3A:
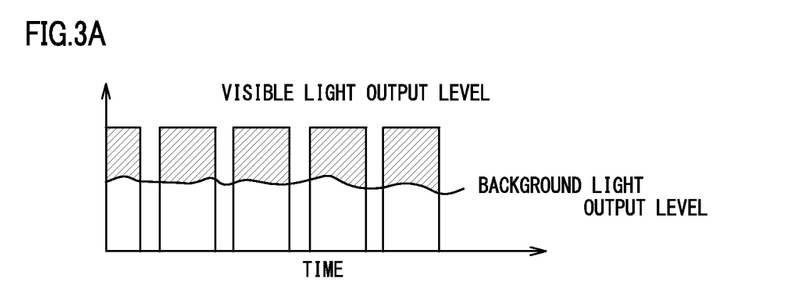
FIGS. 3A and 3B show another method for detecting an output of the visible laser light Ls.
Figure 3B:
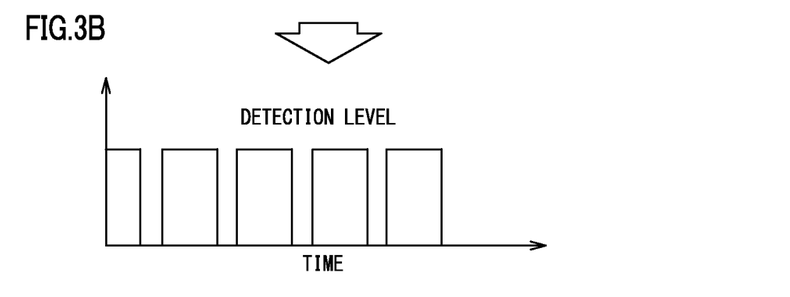

The visible laser light Ls does not need to be continuous and may be pulsed light that is oscillated and caused to exit at a specific pulse cycle. In this case, as shown in FIG. 3A, the detection cycle of detecting an output of the illumination spot S (visible laser light Ls) in the laser light illumination area A and an area close thereto may be synchronized with a pulse cycle of causing the pulsed visible laser light Ls to exit. In this way, as shown in FIG. 3B, a noise component from the background light is removed, and thus the output of the visible laser light Ls is detected more certainly.

Figure 4A:
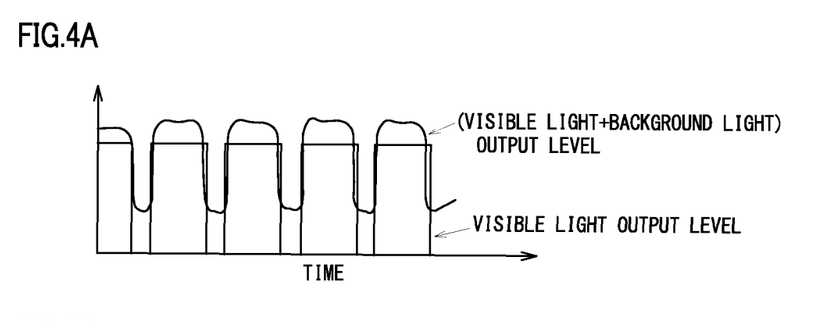
FIGS. 4A and 4B show still another method for detecting an output of the visible laser light Ls.
Figure 4B:
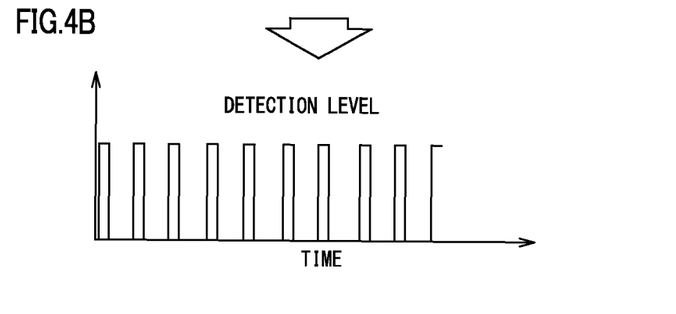

As shown in FIG. 4A, the optical output of the laser light illumination area A and the area close thereto may be detected by the image capturing element 52 when the laser light illumination area A is illuminated with the visible laser light Ls by the visible laser light provision unit 23 at a specific pulse cycle, and when the laser light illumination area A is not illuminated. In this way, the illumination spot S (output of the visible laser light Ls) is detected from the difference between the outputs.

The visible laser light Ls exits from a tip of the laser light waveguide path 40. In the case where the positions of the laser light waveguide path 40 and the image capturing element 52 are fixed to a certain degree and the distance between the exit tip of the laser light waveguide path 40 and the illumination target is kept almost the same, the illumination spot S of the visible laser light Ls is spatially limited to a specific range in the captured image displayed by the image display unit 36.

Thus, as shown in FIG. 5, only the illumination spot S of the visible laser light Ls and the area close thereto is spatially limited by a space filter (aperture) F. In this way, the illumination spot S (visible laser light Ls) is made clearly distinguishable from the background light around the laser light illumination area A.

As described above, the laser device unit 2 includes the laser light provision units (23, 24) that oscillate and cause respective types of laser light to exit, the laser light waveguide path 40 formed of an optical fiber capable of guiding the infrared laser light Li, which is visually unrecognizable, and the visible laser light Ls, which is visually recognizable, and the central control unit 22 that controls the laser light provision units (23, 24). The central control unit 22 detects the illumination spot S (output of the visible laser light Ls) based on a captured image, captured by the image capturing element 52, of the laser light illumination area A and the area close thereto illuminated with the laser light (Li, Ls). Based on the detection result of the illumination spot S (output of the visible laser light Ls), the central control unit 22 controls the exit of the infrared laser light Li by the infrared laser light provision unit 24. Owing to this arrangement, the soundness of the laser light waveguide path 40 that guides the infrared laser light of a high energy output is monitored, so that the infrared laser light exits safely, with a simple structure.

This will be described in more detail. The infrared laser light Li, which is visually unrecognizable, and the visible laser light Ls, which is visually recognizable, are guided by the laser light waveguide path 40. Owing to this arrangement, the visible laser light Ls is directed to a desired position, and thus the infrared laser light Li, which is visually unrecognizable, is prevented from illuminating an unintended position.

The control unit 22 detects the illumination spot S, namely, the output of the visible laser light Ls, based on a captured image, captured by the image capturing element 52, of the laser light illumination area A and the area close thereto illuminated with the laser light (Li, Ls) guided by the laser light waveguide path 40. Due to this arrangement, the soundness of the laser light waveguide path 40 is monitored in real time.

The exit of the infrared laser light Li is controlled based on the detection result of the illumination spot S (output of the visible laser light Ls). Owing to this arrangement, when, for example, the laser light waveguide path 40 is ruptured and is not sound, the output of the visible laser light Ls guided by the laser light waveguide path 40 is not detected. Namely, although the visible laser light Ls is guided together with the infrared laser light Li, which is visually unrecognizable, the output of the visible laser light Ls is not detected. Based on this, the control unit 22 determines that the laser light waveguide path 40 is not sound and thus controls the exit of the infrared laser light Li of a high energy output to be stopped. Therefore, a defect, for example, leak of the infrared laser light Li having a high optical energy, is prevented and the laser light waveguide system 1 is used safely.

As described above, in the laser light waveguide device 2 and the laser light waveguide system 1, the infrared laser light Li, which is of a high energy output and is visually unrecognizable, and the visible laser light Ls, are guided by the laser light waveguide path 40. Thus, the infrared laser light Li is prevented from unexpectedly illuminating an unintended position. In addition, the illumination spot S is detected by use of the image capturing element 52. Therefore, the output of the visible laser light Ls is visually recognized, and thus the soundness of the laser light waveguide path 40 is checked in real time. Therefore, even if some abnormality, for example, breakage, occurs to the laser light waveguide path 40, the exit of the infrared laser light Li of a high energy output is stopped, so that a human or a device located around the laser light waveguide device 2 or the laser light waveguide system 1 is protected against any risk and safety is guaranteed. This is realized with a simple structure with no need to provide any additional device such as a sensor or the like to the laser light waveguide path 40.

The laser light in one or more embodiments of the present invention corresponds to the visible laser light Ls and the infrared laser light Li in the above-described embodiments; and in the same manner, the laser light provision unit corresponds to the visible laser light provision unit 23 and the infrared laser light provision unit 24;

the control unit corresponds to the central control unit 22;

the image capturing unit corresponds to the image capturing element 52;

the laser light waveguide device corresponds to the laser device unit 2;

the laser light waveguide system corresponds to the laser light waveguide system 1; and the illumination unit corresponds to the illumination light source 33.

However, the present invention is not limited to the above-described embodiments, and may be carried out in any of various other embodiments.

In the above description, the laser light waveguide path 40 is inserted into the flexible endoscope 50, and the image capturing element 52 is provided in the vicinity of the tip of the endoscope 50. It is sufficient that the image capturing element 52 captures an image of the laser light illumination area A and the area close thereto. For example, as shown in FIG. 6, the image capturing element 52 may be provided in an endoscope different from the endoscope 50 into which the laser light waveguide path 40 is inserted.

Specifically, as shown in FIG. 6, a hard endoscope 60 may be used that is provided to the laser light illumination area A, from a different space from that of the laser light waveguide path 40, so as to locate the image capturing element 52 proximate to the laser light illumination area A. The present invention is applicable to a surgical operation using the hard endoscope 60.

In the above-described embodiments, the laser light waveguide path 40 is formed of a hollow optical fiber. The present invention is not limited to this. The laser light waveguide path may be formed of a solid optical fiber capable of guiding both of the visible laser light Ls and the infrared laser light Li.

In the above description, the output of the visible laser light Ls is detected, so that the infrared laser light Li is controlled to exit. Alternatively, in the case where the output of the visible laser light Ls is detected but the level of the output is lower than a predetermined threshold level, the exit of the infrared laser light Li may be stopped.

The above description is regarding an endoscope used in the medical field. The present invention is applicable to an industrial endoscope instead of the endoscope used in the medical field.

DESCRIPTION OF THE REFERENCE NUMERALS

1 . . . Laser light waveguide system
2 . . . Laser device unit
22 . . . Central control unit
23 . . . Visible laser light provision unit
24 . . . Infrared laser light provision unit
33 . . . Illumination light source
40 . . . Laser light waveguide path
50 . . . Endoscope
52 . . . Image capturing element
A . . . Laser light illumination area
Li . . . Infrared laser light
Ls . . . Visible laser light

What is claimed is:

1. A laser light waveguide system, comprising:
an infrared laser light output unit that emits invisible infrared laser light;
a visible laser light output unit that emits visible laser light;
an endoscope that includes an image capturing unit at a tip of the endoscope;
a laser light waveguide path formed of an optical fiber capable of guiding both the infrared laser light and the visible laser light and arranged either inside or outside of the endoscope; and
a control unit that controls the infrared laser light output unit and the visible laser light output unit, wherein
the control unit detects an output of the visible laser light based on a captured image, captured by the image capturing unit, of a laser light illumination area and an area close thereto illuminated with the visible laser light, and controls emission of the infrared laser light based on a result of detection of the output of the visible laser light.

2. The laser light waveguide system according to claim 1, wherein the laser light waveguide path is formed of a hollow optical fiber.

3. The laser light waveguide system according to claim 1, further comprising
an illumination unit that illuminates the laser light illumination area and the area close thereto, wherein
the control unit controls the illumination unit, and
the control unit controls an illumination cycle of the illumination unit so as to be synchronized with a detection cycle of detecting the visible laser light based on the captured image of the laser light illumination area and the area close thereto.

4. The laser light waveguide system according to claim 1, further comprising
a filter that attenuates background light around the laser light illumination area.

5. The laser light waveguide system according to claim 1, wherein
the control unit controls the visible laser light to emit at a predetermined pulse cycle, and
the control unit controls a detection cycle of detecting the visible laser light, based on the captured image of the laser light illumination area and the area close thereto, to be synchronized with a pulse cycle of causing the visible laser light to exit.

6. The laser light waveguide system according to claim 1, wherein
the image capturing unit captures the image of the laser light illumination area and the area close thereto illuminated with the visible laser light at a pulse cycle, and
the control unit detects the visible laser light based on a difference between an output of the captured image when the visible laser light is emitted, and an output of the captured image when the visible laser light is not emitted.

7. The laser light waveguide system according to claim 1, wherein the image capturing unit includes a wavelength filter that attenuates light in a visible light wavelength region except for an oscillation wavelength of the visible laser light.

* * * * *